(12) United States Patent
Smith et al.

(10) Patent No.: US 7,594,578 B2
(45) Date of Patent: Sep. 29, 2009

(54) METHOD AND APPARATUS FOR STORING BONE CEMENT COMPONENTS

(75) Inventors: Daniel B. Smith, Warsaw, IN (US); Robert M. Ronk, Pierceton, IN (US); John M. McDaniel, Warsaw, IN (US); Jeffrey L. Colbert, Claypool, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 430 days.

(21) Appl. No.: 11/043,707

(22) Filed: Jan. 26, 2005

(65) Prior Publication Data

US 2006/0226043 A1    Oct. 12, 2006

(51) Int. Cl.
*A61B 19/02* (2006.01)
*B65D 25/14* (2006.01)
*B61B 61/18* (2006.01)

(52) U.S. Cl. .............. 206/438; 53/284.7; 206/219; 206/484; 604/416

(58) Field of Classification Search ......... 206/219–222, 206/438; 383/906, 904; 604/408–416; 366/130, 366/139; 222/107; 53/284.7
See application file for complete search history.

(56) References Cited

U.S. PATENT DOCUMENTS

| | | | | |
|---|---|---|---|---|
| 2,661,741 A | * | 12/1953 | Puckman | 604/408 |
| 2,962,192 A | * | 11/1960 | Volckening | 222/107 |
| 3,520,471 A | * | 7/1970 | Faust | 383/906 |
| 3,882,259 A | * | 5/1975 | Nohara et al. | 428/36.7 |
| 3,983,994 A | * | 10/1976 | Wyslotsky | 206/219 |
| 4,445,550 A | | 5/1984 | Davis et al. | |
| 4,463,875 A | | 8/1984 | Tepic et al. | |
| 4,650,452 A | * | 3/1987 | Jensen | 383/904 |
| 4,772,134 A | * | 9/1988 | Jensen et al. | 383/904 |
| 4,840,017 A | * | 6/1989 | Miller et al. | 53/468 |
| 4,854,737 A | * | 8/1989 | Steer et al. | 604/408 |
| 4,973,168 A | | 11/1990 | Chan | |
| 4,996,848 A | | 3/1991 | Nelson et al. | |
| 5,259,844 A | * | 11/1993 | Bilstad et al. | 604/408 |
| 5,312,189 A | * | 5/1994 | Aeschbach et al. | 383/906 |
| 5,370,221 A | | 12/1994 | Magnusson et al. | |
| 5,398,483 A | | 3/1995 | Smith et al. | |
| 5,588,745 A | | 12/1996 | Tanaka et al. | |
| 5,951,160 A | | 9/1999 | Ronk | |
| 5,957,584 A | * | 9/1999 | Lakey | 383/906 |

(Continued)

FOREIGN PATENT DOCUMENTS

EP    0768067    4/1997

(Continued)

OTHER PUBLICATIONS

Partial European Search Report mailed Mar. 31, 2006 for EP 06250308.

(Continued)

*Primary Examiner*—Bryon P Gehman
(74) *Attorney, Agent, or Firm*—Harness, Dickey

(57) ABSTRACT

A container for storing a liquid component of bone cement. The container includes a flexible film sealed about its periphery to define a cavity. The cavity has a first layer, a second layer, and a vinyl barrier layer between the first layer and the second layer. The cavity is operable to store the liquid component of bone cement.

28 Claims, 3 Drawing Sheets

U.S. PATENT DOCUMENTS 5,961,210 A 10/1999 McCardel et al.
5,997,544 A 12/1999 Nies et al.
6,286,670 B1 9/2001 Smith

FOREIGN PATENT DOCUMENTS

| EP | 1 153 846 | 11/2001 |
| EP | 1466572 | 10/2004 |
| WO | WO99/67015 | 12/1999 |

OTHER PUBLICATIONS

European Search Report mailed Aug. 9, 2006 for EP 06250308.

\* cited by examiner

METHOD AND APPARATUS FOR STORING BONE CEMENT COMPONENTS

FIELD OF THE INVENTION

The present invention relates to methods and apparatuses for packaging bone cement components. In particular, the present invention relates to methods and devices for individually packaging different bone cement components.

BACKGROUND OF THE INVENTION

The natural joints of the human body often undergo degenerative changes due to various etiologies. When these degenerative changes are advanced, irreversible, and unresponsive to non-operative management, it may ultimately become necessary to replace the natural joint with a prosthetic device. When such replacement becomes necessary, the prosthetic device that is implanted is often secured to the natural bone using bone cement.

Bone cement that is used to secure prosthetic devices to bone is generally comprised of a liquid monomer component that polymerizes about a polymeric powder component. In this regard, bone cement is generally formed from a methyl methacrylate monomer and poly (methyl methacrylate) or methyl methacrylate-styrene homo- or copolymer. The polymeric powder component of bone cement can comprise particles composed of spherical beads that may be obtained by a suspension polymerization process. The beads are generally sieved to comply with particular size specifications. The powder component may also comprise particles that have been milled or crushed.

The preparation of bone cement generally involves mixing the polymer and monomer components in a suitable reaction vessel to form the bone cement. Generally, it is necessary that the components of bone cement be uniformly and thoroughly mixed so that a homogenous product is obtained. Increased homogeneity of the blend and minimal porosity are particularly desirable in providing a cement mixture that is easy to work with, yet maintains satisfactory mechanical properties. In producing bone cement it is crucial to maintain the liquid and the powder components separate until just prior to use and to avoid exposure of the components to the atmosphere because of the potentially malodorous and volatile nature of the bone cement components.

To keep the liquid and powder components separate, the two components are often stored in individual containers or packages. The liquid component is often stored in a glass ampoule and the powder component is often stored in a plastic pouch. While existing containers for the liquid and powder components are useful for their intended purposes, they are subject to improvement.

SUMMARY OF THE INVENTION

In one embodiment the present invention provides for a container for storing a liquid component of bone cement. The container includes a sealed cavity defined by a flexible film. The cavity is operable to store the liquid component of bone cement.

The present invention further provides for a method of manufacturing a container for storing a liquid component of bone cement. The method includes the following steps: sealing a first flexible film to a second flexible film to form a cavity between the first flexible film and the second flexible film, each of the first flexible film and the second flexible film at least substantially impermeable to the liquid component of bone cement, the cavity having an opening between the first flexible film and the second flexible film; filling the cavity with the liquid component of bone cement by injecting the liquid component through the opening; and sealing the opening.

The present invention still further provides for a kit for storing a monomer component of bone cement and a polymeric component of bone cement. The kit includes a first flexible container and a second flexible container. The first flexible container is for storing the monomer component and is impermeable to the monomer component. The second flexible container is for storing the polymeric component and is at least partially impermeable to moisture.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figures 1, 2:
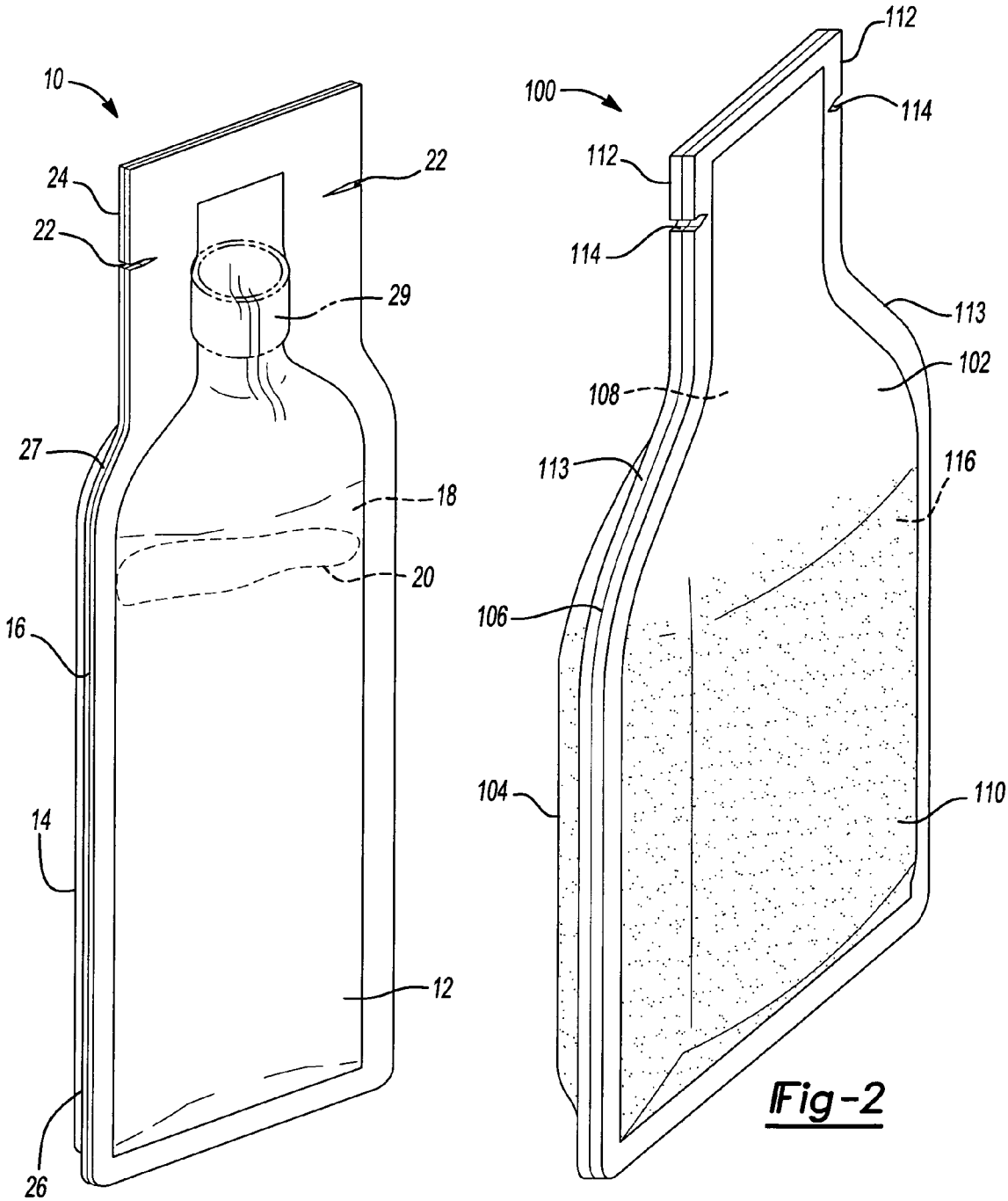
FIG. 1 is a perspective view of a first container of the present invention.
FIG. 2 is a perspective view of a second container of the present invention.

FIG. 1 illustrates a first container 10 of the present invention. The first container 10 generally includes a front panel 12 and a rear panel 14. The panels 12 and 14 are each made of a generally impervious flexible film, which is fully described below. The panels 12 and 14 can each be formed from a single sheet of flexible film with each sheet sealed to the other at a seal 16. The seal 16 can be any impermeable seal, but is typically a heat seal and is further described below. The seal 16 defines a first interior cavity 18 between the front panel 12 and the rear panel 14. The panels 12 and 14 need not each be formed of a single flexible sheet, but can take various other forms. For example, the panels 12 and 14 can be formed from a single flexible sheet that is folded at one or more points and sealed to define the cavity 18. While the first container 10 is shown as being substantially rectangular, the present invention is applicable to flexible containers of other shapes, such as square, triangular, or trapezoidal. The container 10 can have curved edges, as illustrated, or it can also have more angular edges.

The first interior cavity 18 is suitable for storing a variety of different materials, such as, a liquid monomer component of bone cement 20. The liquid monomer component 20 can be a variety of different materials in a variety of different forms.

For example, the liquid monomer 20 can be a methyl methacrylate monomer liquid. In addition, a polymerization accelerator, such as about 0.5% to about 4% dimethyl-para-toluidine can be used. Further, a stabilizer in monomer hydroquinone at 10-100 ppm can be used. Optionally, the first interior cavity 18 can also include any suitable antibacterial agent.

To provide easy access to the contents of the first interior cavity 18, the first container 10 can include a slit 22, which can take the form of a pre-cut portion that partially extends through the seal 16 and through both the front and rear panels 12 and 14. The slit 22 can be located at most any point in the seal 16, such as at or near a neck 24 of the first container 10. The slit 22 facilitates cutting and/or tearing of the front and rear panels 12 and 14 to gain access to the first interior cavity 18. At the slit 22 the rear panels 12 and 14 can be cut in any suitable manner, such as by using a cutting instrument or by tearing the first container 10.

The neck portion 24 of the first container 10 is generally more narrow than a main body 26 of the first container 10, as viewed in FIG. 1. Between the neck 24 and the main body 26, the first container can include a tapered portion 27 having a generally tapered shape to channel the contents of the first interior cavity 18 to the neck portion 24. The tapered portion 27 and the neck portion 24 also facilitate deposition of contents within the first interior cavity 18. Between the tapered portion 27 and the slit 22 can be an optional stent 29, or any other suitable support structure to expand the distance between the panels 12 and 14 and facilitate passage of the monomer 20 through the neck portion 24. The stent 29 typically can be an inert, rigid, or semi-rigid cylinder and can include an opening at its center to permit passage of the monomer 20. The stent 29 can be made of any suitable material, such as polyethylene.

The composition of the generally impervious flexible films of the front and rear panels 12 and 14 generally depends upon the nature of the material(s) to be stored in the cavity 18 and the conditions under which the material(s) will be used. For example, for many applications and materials, such as storage of the liquid monomer component 20 of bone cement, the panels 12 and 14 can be made of Cryovac® T60XXB series material, such as Cryovac® T6040B or T6050B material, which is manufactured by Sealed Air Corporation of Saddle Brook, N.J. Cryovac® T60XXB series material is a multi-layered material that generally includes, in part, the following layers in the order listed: a linear low density polyethylene heat seal adhesive (LLDPE) inner layer, a first adhesive, a first nylon layer, an ethyl vinyl alcohol copolymer barrier layer (EVOH), a second nylon layer, a second adhesive, and a polypropylene outer layer. In addition to Cryovac® T60XXB series material, any flexible film having at least a low permeability to the liquid monomer component 20 of bone cement, such as methyl methacrylate, can be used. Further, any flexible film having low elutables and extractables and that is compatible with the liquid monomer component 20 such that the monomer 20 does not negatively impact the film and vice versa, can be used. Still further, any other sealable flexible film having adequate barrier properties can be used.

With additional reference to FIG. 2, a second container according to the present invention is illustrated. The second container 100 generally includes a front panel 102 and a rear panel 104. The panels 102 and 104 are each generally made of a flexible film, which is further described below, and are sealed together at a seal 106. The seal 106 defines a second interior cavity 108 between the front panel 102 and the rear panel 104. While the second container 100 is shown as being substantially rectangular, the present invention is applicable to flexible containers of other shapes, such as square, triangular, or trapezoidal. Further, the second container 100 can have curved edges, as illustrated, or angular edges.

The second container 100 generally includes a main body 110 and a neck 112. As illustrated, the neck 112 can be more narrow than the main body 110. Between the neck 112 and the main body 110 can be a tapered portion 113 to facilitate directing the material into and out of the second interior cavity 108.

To facilitate access to the contents of the second interior cavity 108, the second container 100 can include a slit 114, which can take the form of a pre-cut portion in the seal 106 that extends through both the front and rear panels 102 and 104. The slit 114 can be located at any position within the seal 106, such as at the neck portion 112. At the slit 114 access to the second cavity 108 can be obtained in any suitable manner, such as by using a cutting instrument to cut through the seal 106 or by tearing a small portion of the seal 106 to separate the front panel 102 and the rear panel 104.

The panels 102 and 104 can be made of any generally flexible film that is at least partially impermeable to moisture. For example, the panels 102 and 104 can be made of Cryovac® T60XXB series film material, such as Cryovac® T6050B. Further, the panels 102 and 104 can be made of any suitable polyethylene. The exact composition of the front and rear panels 102 and 104 depends upon the nature of the material(s) to be stored within the second cavity 108 and the conditions under which the second container 100 will be used and stored.

The second cavity 108 is suitable for storing a variety of different materials, such as a polymeric powder component of bone cement 116. The polymeric powder 116 can be of a variety of different materials in a variety of different forms. For example, the polymeric powder can be a poly (methyl methacrylate) or methyl methacrylate-styrene homo- or copolymer. The polymeric powder component 116 can comprise various other forms or morphologies, such as spherical beads that can be obtained by any conventional suspension polymerization process. The beads can be sieved to comply with particular size specifications. The powder component can also comprise particles that have been milled or crushed, such as benzoyle peroxide at about 1% to about 5% and radiopacifiers, such as barium sulfate and zircronum dioxide, at at least about 75% to about 30%. Optionally, the second cavity 108 can further include any suitable antibacterial agent and any other suitable drug. In some applications the second interior cavity 108 can be vacuum sealed, but a vacuum seal is not necessary in all applications.

The manufacture of the first and second containers 10 and 100 will now be described in detail. With respect to the first container 10, the panels 12 and 14 can comprise various different flexible films. For exemplary purposed only, the panels 12 and 14 are now described as Cryovac® T6040B or T6050B flexible films.

Figure 3:
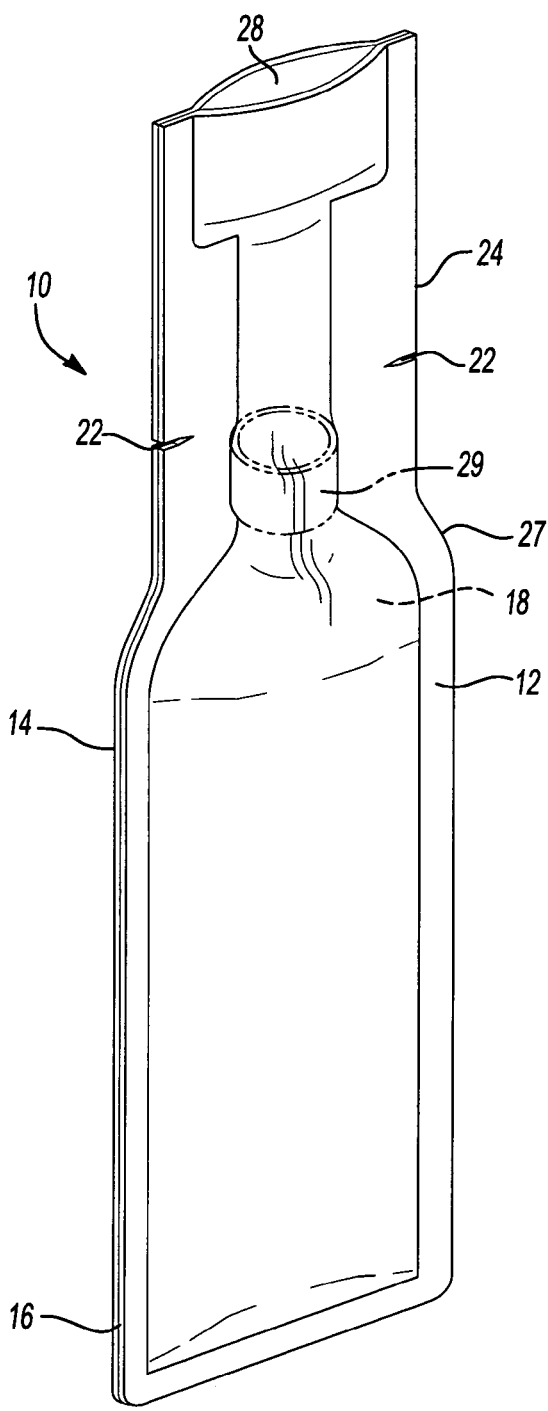
FIG. 3 is a perspective view of the first container of FIG. 1 during manufacturing.

The Cryovac® films are typically individually provided by the manufacturer in the form of large sheets of material on a roll. Two sheets of Cryovac® film are cut from the roll and orientated such that the inner LLDPE layers face each other. With additional reference to FIG. 3, the two Cryovac® films are sealed together in the region of the seal 16 using any suitable sealing method or process, such as any suitable heat seal process, to form the seal 16. However, at this point in the manufacturing process the first container 10 is only sealed on three sides and is not sealed in the area of the neck 24 to define an aperture 28, which provides access to the first interior cavity 18. Optionally, one sheet of Cryovac® film can be used and folded to define the first interior cavity 18 and the aperture 28.

Figure 4:
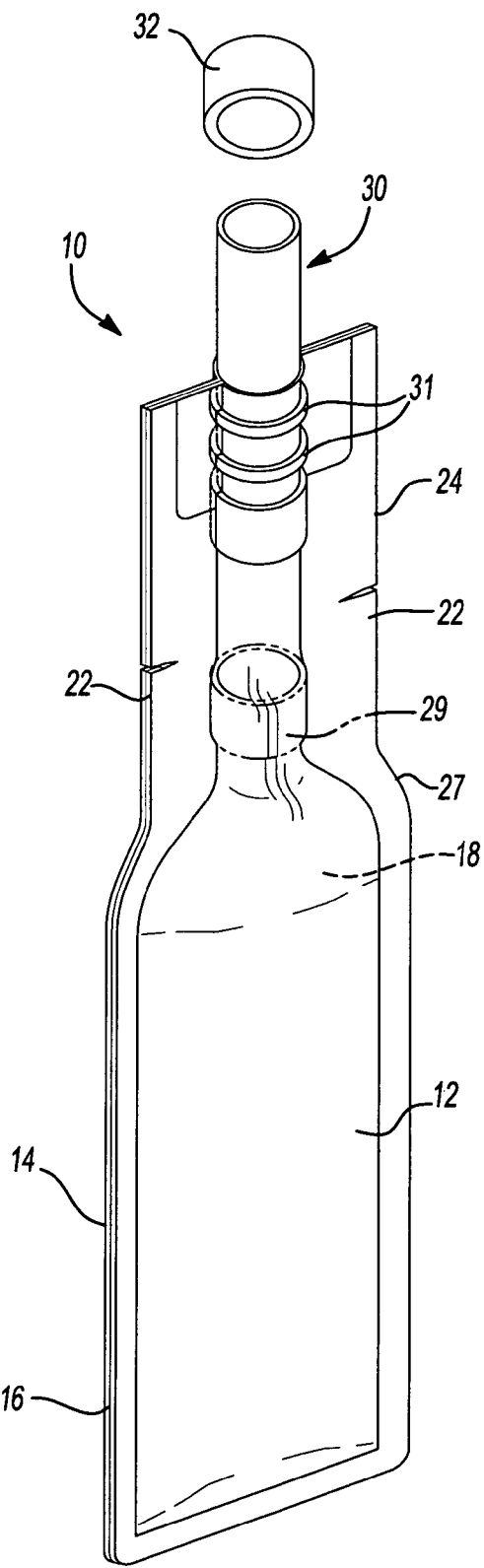
FIG. 4 is a perspective view of the first container of FIG. 1 during manufacturing.

The stent 29 may be inserted within the aperture 28 at the area between the slit 22 and the tapered portion 27. With additional reference to FIG. 4, a port 30 is inserted within the aperture 28 to assist filling of the first interior cavity 18. The port 30 is typically a flexible tube having an outer polymer surface that facilitates securing the port 30 within the aperture 28 through heat sealing. However, the port 30 can be any suitable device to provide communication between the first interior cavity 18 and the outer atmosphere.

The stent 29 and the port 30 are sealed within the aperture 28 at the neck 24 using any suitable process, such as heat sealing, to seal the stent 29 and the port 30 between the front panel 12 and the rear panel 14 and to close the aperture 28. For example, the exterior surface of the stent 29 can be fused with the inner surface of the neck 24. Alternatively, the stent 29 can be held in position due to friction between the stent 29 and the neck 24 at a portion of the neck 24 having the same diameter of the neck 24 or the seal 16 can include a recess or pocket in the neck 24 to receive the stent 29. The port 30 can include one or more ribs 31 that cooperate with the panels 12 and 14 to help secure the port 30 between the panels 12 and 14. The port 30 extends from outside of the first container 10 to within the first interior cavity 18. A cap 32 is press fit over the port 30 to close the port 30. In some applications, the cap 32 is a silicone cap that can be punctured by, for example, a syringe to facilitate filling the first interior cavity 18.

Figure 5:
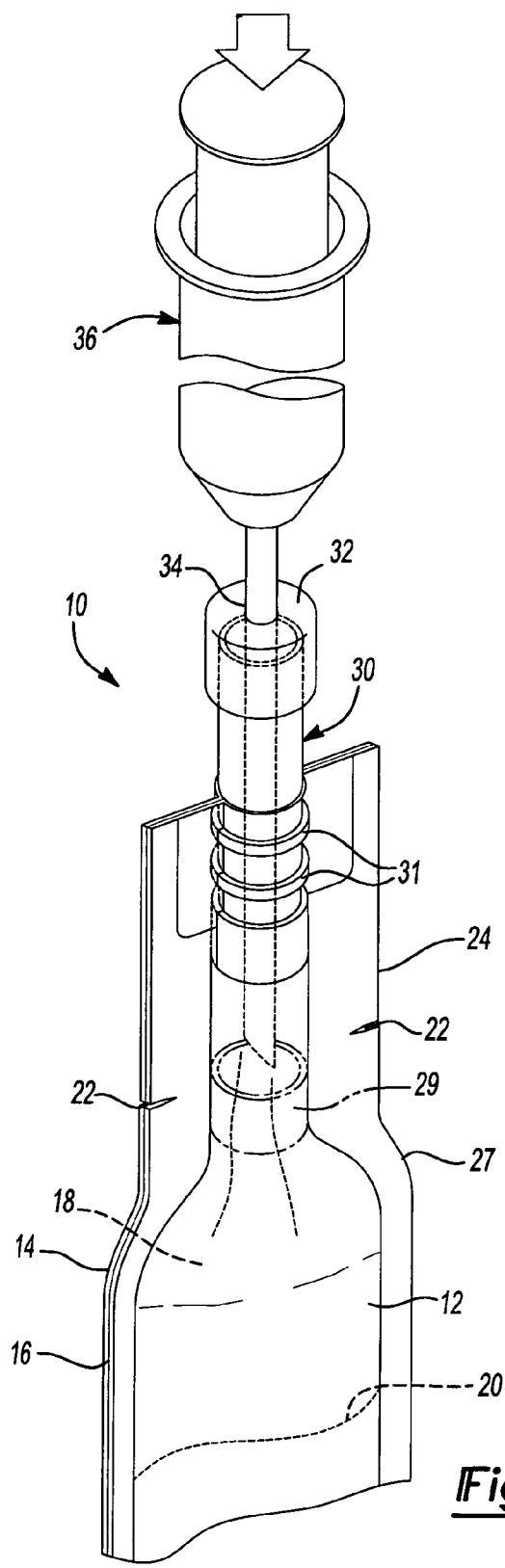
FIG. 5 is a perspective view of the first container of FIG. 1 during manufacturing.

With the port 30 and the cap 32 in place, the inner cavity 18 is sterilized by any suitable process and then filled with the desired material, which is previously sterilized itself by a sterile process, such as sterile filtration. The inner cavity 18 is filled with the sterilized material under aseptic conditions. Most any suitable sterilization process can be used, such as electron beam and/or gamma sterilization. With additional reference to FIG. 5, a cannula or a needle 34 of a syringe 36 containing the liquid component 20 can be inserted through the cap 32 and into the port 30 to inject the liquid component 20, for example, into the cavity 18.

Figure 6:
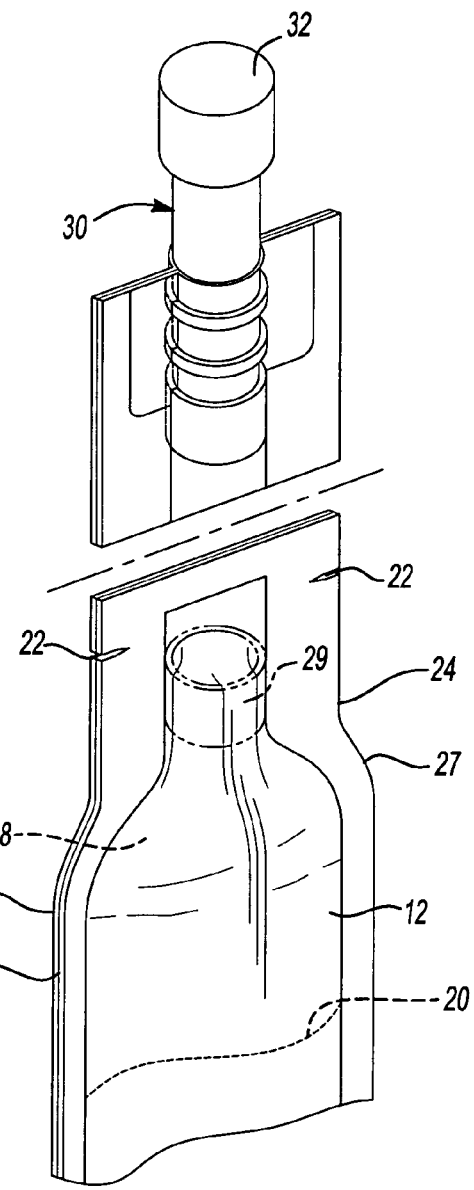
FIG. 6 is a perspective view of the first container of FIG. 1 during manufacturing.

After the inner cavity 18 is filled with the liquid material 20, the unsealed portion of the front and rear panels 12 and 14 at the neck 24 and beneath the port 30 is sealed using any suitable heat seal process. Heat sealing the neck 28 just below the port 30 closes the inner cavity 18 to the outer atmosphere. As illustrated in FIG. 6, the portion of the neck 24 having the port 30 and the cap 32 is removed from the first container 10 using any suitable cutting device or process. The exterior surface of the filled first container 10 is again sterilized using any suitable sterilization technique to sterilize the outer surface of the first container 10, such as gas sterilization.

At most any point during the manufacturing process of the first container 10 described herein, the slit 22 can be made within the neck 24 or at any other suitable location within the first container 10. For example, the slit 22 can be made before or after the portion of the neck 24 that includes the port 30 is removed. The slit 22 can be made using most any suitable technique or process, such as by cutting the front and rear panels 12 and 14 with a sharp edge or scissors.

The second container 100 can be manufactured using substantially the same processes and methods described above to manufacture the first container 10 or any other suitable manufacturing process and technique. One of ordinary skill in the art will readily recognize how the process of manufacturing the first container 10 is applied to manufacture the second container 100. The second container 100 can be any suitable pouch that is at least generally impermeable to moisture.

The contents of the first and second containers 10 and 100 can be used in a variety of different ways. For example, in applications where the first container 10 contains the liquid monomer component 20 of bone cement and the second container 100 contains the polymeric powder component 116 of bone cement, the first container 10 and the second container 100 are both opened in any suitable manner, such as by tearing the containers 10 and 100 across the slits 22 and 114. The contents of the containers 10 and 100 are placed in a suitable container, such as a mixing bowl or vacuum mixing cartridges, where the components 20 and 116 are processed using conventional techniques to obtain bone cement. During this processing, various other components can be added to the monomer 20 and the polymer 116, such as suitable antibiotics. The bone cement can be implanted in patients using known techniques to facilitate the fixation of implants and/or bone, as well as the healing process in general.

The first and second containers 10 and 100 can be sold individually or together as a package. The containers 10 and 100 provide numerous advantages over existing containers. For example, the first container 10 provides a safe and easy to use package for the liquid monomer component 20 of bone cement. The first container 10 is easier to handle and ship then conventional glass ampoules. The first and second containers 10 and 100 include tapered necks to facilitate the removal and insertion of contents within the first interior cavity 18 and the second interior cavity 108 respectively. The second container 100 protects the contents of the interior cavity 108 because it is at least substantially impermeable to moisture. Also, the first and second containers 10 and 100 can be filled and sealed without using an open flame.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A container for storing a liquid component of bone cement comprising:
    a flexible film sealed about its periphery to define a cavity, said flexible film includes an inner layer, an outer layer, a vinyl barrier layer between said inner layer and said outer layer, a first nylon layer between said inner layer and said vinyl barrier layer, and a second nylon layer between said outer layer and said vinyl barrier layer, said cavity includes:
    a neck portion having a sealed end;
    a main body portion having a width that is larger than said neck portion;
    a stent extending from a first terminal end to a second terminal end and seated in said neck portion to facilitate withdrawal of the liquid component of bone cement from said cavity, said stent extending from said first terminal end to said second terminal end only within less than an entirety of said neck portion and is proximate to said sealed end, said stent permits passage of the liquid component of bone cement there through; and
    the liquid component of bone cement.

2. The container of claim 1, wherein said flexible film includes a front flexible film panel and a rear flexible film panel, said front flexible film panel is sealed to said rear flexible film panel;
    wherein said stent is seated between said front flexible film panel and said rear flexible film panel to separate said front flexible film panel from said rear flexible film panel.

3. The container of claim 1, wherein said flexible film is selected from Cryovac® T60XXB series film.

4. The container of claim 1, wherein said cavity includes a tapered portion between said neck portion and said main body portion.

5. The container of claim 1, wherein said stent includes a hollow, cylindrical tube.

6. A container for storing a liquid component of bone cement comprising:
   a flexible film sealed about its periphery to define a cavity, said flexible film including:
      an inner layer;
      an outer layer;
      a vinyl barrier layer between said inner layer and said outer layer;
      a first nylon layer between said inner layer and said vinyl barrier layer;
      a second nylon layer between said outer layer and said vinyl barrier layer: and
   the liquid component of bone cement stored within said cavity.

7. The container of claim 6, wherein said inner layer includes linear low density polyethylene.

8. The container of claim 6, wherein said flexible film is selected from Cryovac® T60XXB series material.

9. The container of claim 6, wherein said flexible film includes Cryovac® T6050B material.

10. The container of claim 6, wherein said flexible film includes a single sheet of flexible material that is folded at least at one point to define said cavity.

11. The container of claim 6, wherein said container has a tapered portion at least proximate to a neck portion.

12. The container of claim 11, wherein said flexible film includes a pre-cut portion at said neck portion.

13. The container of claim 11 further comprising a stent in said neck portion.

14. The container of claim 11, wherein said stent includes a hollow, cylindrical tube.

15. The container of claim 6, wherein said cavity has a neck portion, a main body portion, and a tapered portion between said neck portion and said main body portion, said container further comprising:
   a stent that extends only within said neck portion;
   a port that is seated in said neck portion to facilitate insertion of the liquid component into said cavity, said port extends from within said cavity, said stent is confined to an area between said port and said main body portion;
   wherein said cavity is operable to store the liquid component of bone cement.

16. The container of claim 6, further comprising:
   a neck portion of said cavity;
   a main body portion of said cavity having a width that is larger than said neck portion; and
   a stent seated in said neck portion to facilitate withdrawal of the liquid component of bone cement from said cavity, said stent extends only within said neck portion and is proximate to said sealed end, said stent permits passage of the liquid component of bone cement there through.

17. The container of claim 16, further comprising a port that cooperates with a delivery device to facilitate insertion of the liquid component of bone cement into said cavity, said port is separate from said stent.

18. The container of claim 6, wherein said outer layer includes polypropylene.

19. The container of claim 6, further comprising positioning a first adhesive between said inner layer and said first nylon layer; and
   a second adhesive between said outer layer and said second nylon layer.

20. The container of claim 6, wherein said vinyl barrier layer includes ethylene vinyl alcohol.

21. A method of filling a container with a liquid component of bone cement comprising:
   mounting a stent and a port in a neck portion of the container, the neck portion having a width that is smaller than a main body portion of the container, the stent is between the main body portion and the port, the port extends from the container;
   loading the liquid component of bone cement into the main body portion through the port and the stent;
   sealing the neck portion between the port and the stent; and
   separating the port from the container.

22. The method of claim 21, further comprising sealing a front flexible film panel to a rear flexible film panel to form the container.

23. The method of claim 21, further comprising forming the container with a flexible film.

24. The method of claim 23, wherein the flexible film includes Cryovac® T60XXB series film.

25. The method of claim 23, wherein the flexible film includes an ethylene vinyl alcohol barrier layer and a nylon layer on each side of the ethylene vinyl alcohol barrier layer.

26. The method of claim 21, wherein loading the liquid component of bone cement includes loading methyl methactylate monomer into the main body portion.

27. The method of claim 21, wherein the stent includes a hollow, cylindrical tube.

28. The method of claim 21, wherein the port includes a hollow, cylindrical tube.

* * * * *